United States Patent
Hyson

[11] Patent Number: 5,700,238
[45] Date of Patent: Dec. 23, 1997

[54] DEVICE AND METHOD FOR TREATMENT OF HEADACHE

[76] Inventor: Morton Isaac Hyson, 2020 Goldring #402, Las Vegas, Nev. 89106

[21] Appl. No.: 686,019

[22] Filed: Jul. 25, 1996

[51] Int. Cl.⁶ ............................ A61F 13/12; A61M 35/00
[52] U.S. Cl. .................. 602/74; 604/294; 604/303; 128/858
[58] Field of Search .................. 604/289, 290, 604/294, 304, 305, 303; 128/858; 602/74

[56] References Cited

U.S. PATENT DOCUMENTS

| | | |
|---|---|---|
| 699,897 | 5/1902 | Ray . |
| 924,596 | 6/1909 | Blashfield . |
| 1,150,526 | 8/1915 | Leitheiser . |
| 1,250,273 | 12/1917 | Brady . |
| 1,324,975 | 12/1919 | Morris . |
| 1,481,354 | 1/1924 | Dingfeld ........................ 602/74 |
| 1,607,717 | 11/1926 | Nagler et al. ................. 602/74 |
| 1,642,661 | 9/1927 | Robinson . |
| 1,758,764 | 5/1930 | Roxburg . |
| 1,823,686 | 9/1931 | Hanke . |
| 2,101,628 | 12/1937 | Padelford ..................... 604/294 |
| 2,543,104 | 2/1951 | Golding ........................ 604/294 |
| 3,092,103 | 6/1963 | Mower .......................... 602/74 |
| 4,117,842 | 10/1978 | Hutchins . |
| 4,473,370 | 9/1984 | Weiss ............................ 604/294 |
| 4,632,104 | 12/1986 | Conrow . |
| 4,677,974 | 7/1987 | Leonardi ...................... 602/74 |
| 4,790,031 | 12/1988 | Duerer .......................... 128/858 |
| 4,976,705 | 12/1990 | Aki et al. ...................... 604/304 |

*Primary Examiner*—John G. Weiss
*Assistant Examiner*—David J. Cho
*Attorney, Agent, or Firm*—Quirk & Tratos

[57] ABSTRACT

A device, for treating ailments such as headaches and the like, includes a wrap with an opaque segment adapted to cover the eyes, supraorbital and infraorbital region when the wrap is disposed around the head and tightened. Regions loaded with a medicament such as a skin applied analgesic, anesthetic or balm are disposed on the segment to contact the eyes, supraorbital and infraorbital region areas, the regions dispensing their medicament to the contacted areas.

11 Claims, 2 Drawing Sheets

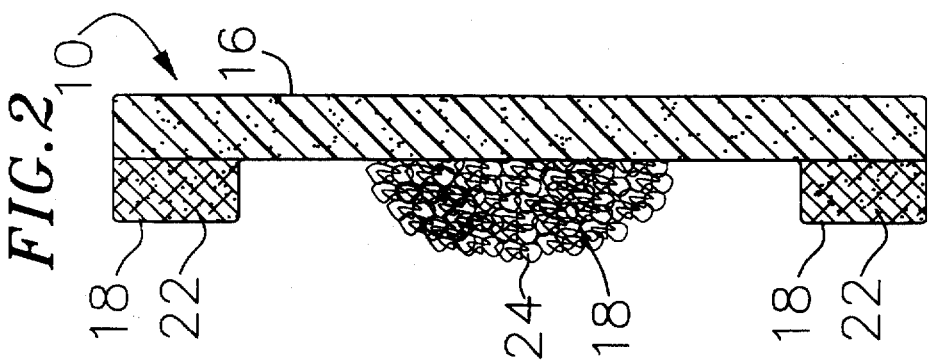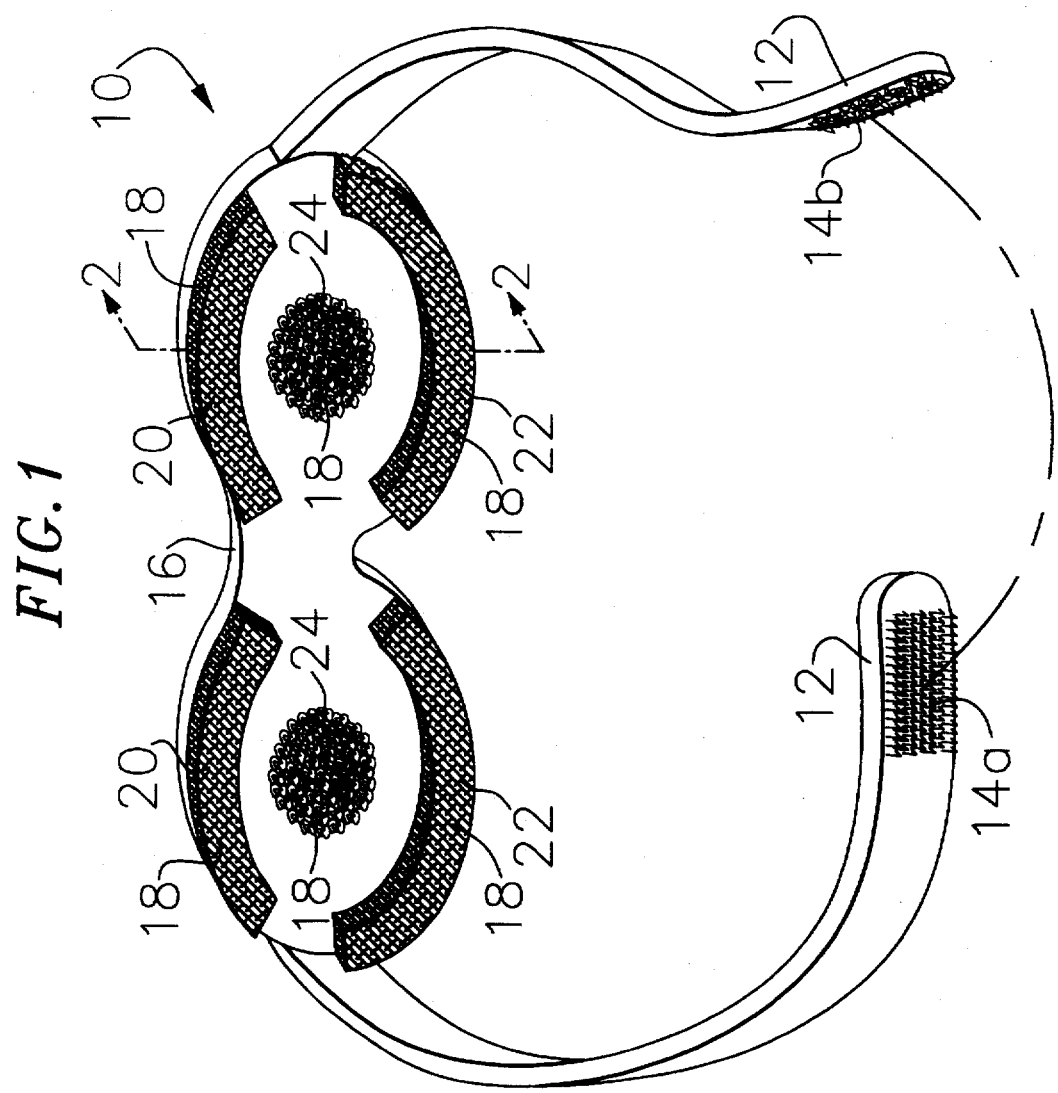

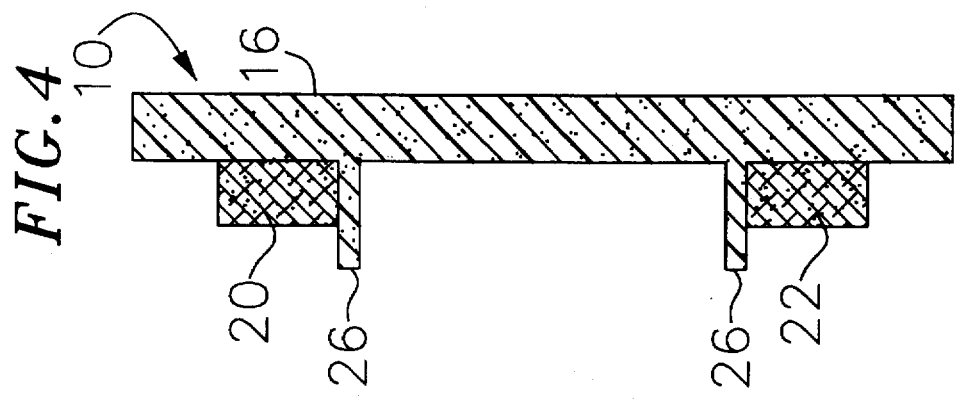
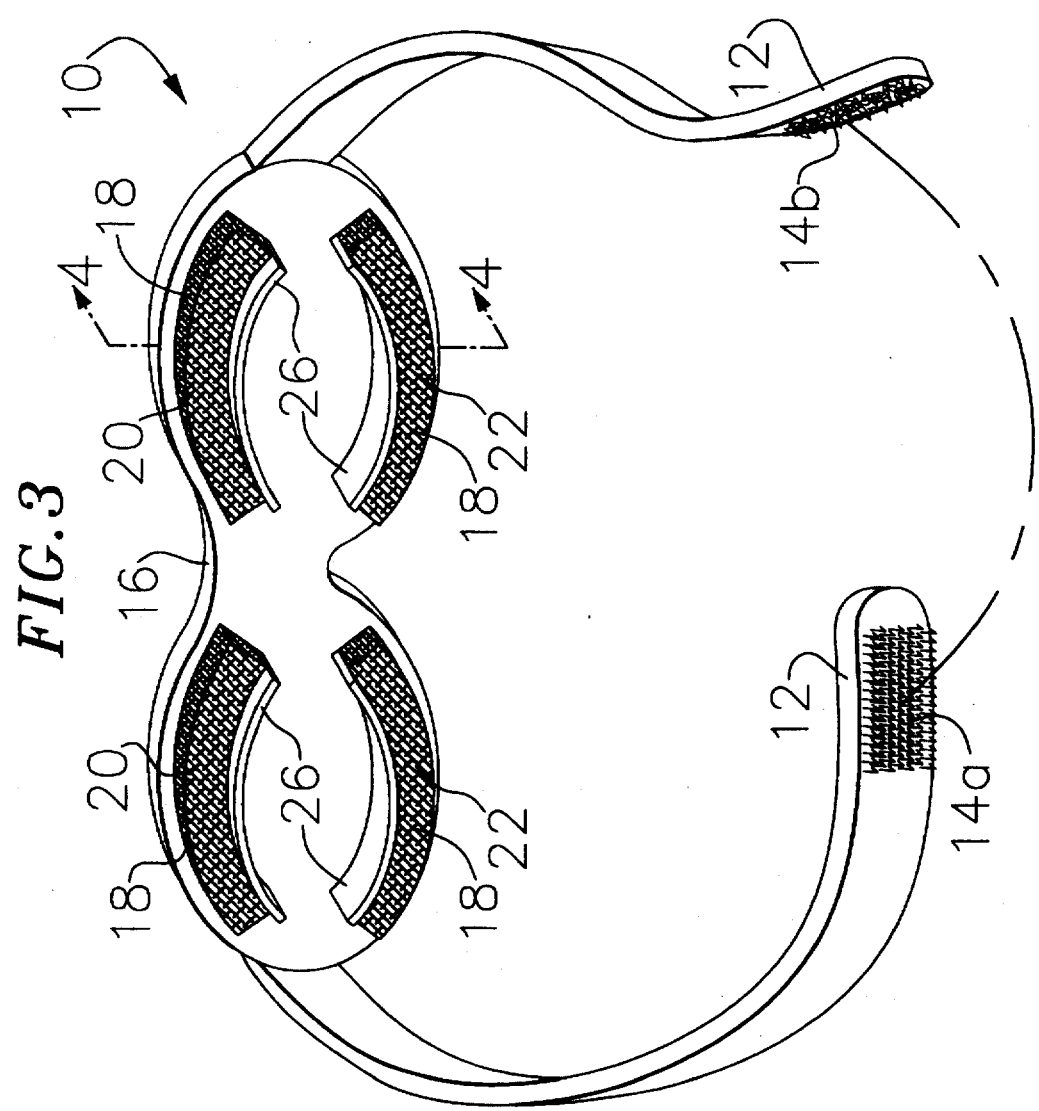

DEVICE AND METHOD FOR TREATMENT OF HEADACHE

FIELD OF THE INVENTION

The present invention relates to devices and methods for treatment of ailments particularly headaches.

BACKGROUND OF THE INVENTION

Many people suffer from ailments such as headaches, migraine headaches, chronic eye strain and sinus maladies. Common symptoms of these ailments are photosensitivity, pain and discomfort. It has been found that the pain associated with these ailments is often localized at the supraorbital region areas which are at and just above the eyebrows, infraorbital region areas defined by the arcuate area below the eyes from the side of the nose to the top of the cheek bone and in the eyes and eye sockets themselves. For severe headaches and sinus maladies, the pain can be debilitating.

Often treatment of these symptoms, when not contra indicated, includes having the patient ingest pain medications such as aspirin, ibuprofen, other prescription and over the counter medicines. It is often some relief to the patient to also block light in view of the photosensitivity. Heat and ice are sometimes prescribed, as well, to treat these symptoms. Some patients have also found that pressure applied to the cranium, at the pain points with the fingers, is also helpful.

A drawback related to ingestion of pain medication is that it subjects the entire body and body chemistry to the effects thereof. The pain medication may cause side effects such as drowsiness, stomach and other gastric problems. Further, some patients may be allergic to such medications.

There is therefore a need for a device and method which can treat such symptoms through the use of skin applied analgesics, anesthetics or other soothing medicaments, addresses photosensitivity and which can, if desired, provide pressure in an attempt to alleviate the pain.

SUMMARY OF THE INVENTION

There is, therefore, provided according to the present invention, a device for treating human ailments which includes a wrap adapted to be disposed around the head, the wrap including an opaque segment adapted to be positioned to overlay the eyes, supraorbital and infraorbital region areas when the wrap is disposed about the head. Means are provided for securing and for tightening the wrap about the head when the segment is appropriately positioned. Regions are disposed on the segment and arranged to be located, when the wrap is secured to the head, to contact at least one of an area proximate to the supraorbital region, an area proximate to the infraorbital region, the nose and the eyes. At least one of the regions includes a medicament adapted to treat the contacted area with a skin applied analgesic, anaesthetic, balm, linament or other compound. In one embodiment, barriers are provided to resist the flow of any medicament from the regions to the eyes. Still further, regions may be provided on the segment to overlay the closed eyes and may include water or other soothing medicament to address eye strain and pain.

The method includes providing a wrap of the type described above and positioning the wrap to locate the segment over the eyes. The wrap is tightened to exert pressure around the head, the tightening urging the medicament contained in the regions to be dispensed to the contacted areas for treatment thereof.

The opaque segment blocks light which, in cooperation with the pressure exerted by tightening of the wrap and the medicaments provided in the regions of the segment, cooperates to treat the symptoms without requiring the patient to ingest medicines.

The device and method can be used alone or in combination with injected or ingested medication.

BRIEF DESCRIPTION OF THE DRAWINGS

These and other features and advantages will become better appreciated with reference to the specification, claims and drawings wherein:

FIG. 1 is an inside view of a device according to the present invention;

FIG. 2 is a section view of the segment for the wrap of FIG. 1 taken along line 2—2;

FIG. 3 is an inside view of a further embodiment of the device according to the present invention; and FIG. 4 is a section view of the segment of the device of FIG. 3 taken along lines 4—4 thereof.

DETAILED DESCRIPTION OF THE PREFERRED EMBODIMENT

Turning to the drawings, FIG. 1 illustrates one embodiment of the device according to the present invention. The device is embodied as a wrap 10 which is adapted to be disposed above the patient's head and secured. The wrap 10 includes free ends 12 and fastening means illustrated as a cooperating hook and pile fastener 14a,b. It is to be understood that any other suitable type of fastener such as a tie, buckle or cooperating snap fastener could also be used.

The wrap 10 includes a segment 16 which may be located intermediate of the ends 12 and is sized and located to, when the wrap 10 is positioned about the head, overlay and contact the eyes and areas there around. As shown, the segment 16 may have a figure-8 shape and a size to overlay the eye sockets, bridge of the nose, sides of the nose, supraorbital region (regions at and above the eyebrows) and infraorbital areas (an arcuate area from the side of the nose, below the eyes and to the cheek bones). To accommodate various ages of patients, the wrap 10 and segment 16 may be in various sizes such as to accommodate adults and children.

The segment 16 includes at least one and preferably a plurality of regions 18 each positioned to contact areas of the face or eyes when the wrap 10 is positioned and secured. Regions 18 include first regions 20 located on the segment 16 to contact the supraorbital region areas above the eyebrows, second regions 22 adapted to contact the infraorbital region areas and third regions 24 to overlay the eyes and eye sockets. Each of the regions 20–24 is preferably fabricated from resilient and absorbent material such as cotton, gauze, sponge, or foam rubber and is suitably adhered to the inside surface of the segment 16 by an adhesive.

Each of the regions 18 is adapted to retain a medicament which may be an analgesic, anaesthetic, balm, water, suave, linament, relaxant or other skin applied medicament or application adapted to treat the patient's symptoms. For example, if the patient is suffering from migraine headaches, the first and second regions 20–22 could contain an analgesic such as Trolamine Salicylate commonly used to treat muscle soreness in sports creams, aspirin creams or a suitable skin applied anaesthetic or a combination thereof. The third regions 24 could contain water or a soothing balm adapted to be applied over the eyes. Alternatively if the patient is suffering from sinus pain, the first regions 20 would contain an analgesic of the type described above with the second regions 22 including a balm such as the type sold by Proctor and Gamble under the trademark VICKS® Vapor Rub. The third regions 24 would contain a soothing eye balm. It is to be understood that the regions 18 could contain any other suitable, skin applied medicament.

The method, according to the present invention, includes providing the wrap 10 of the type described above and positioning it on the head such that the segment 16 overlays the eyes. The wrap 10 is thereafter tightened and the ends 12 fastened by fasteners 14a,b such that the wrap 10 is constricted about the head to exert pressure thereon.

The first through third regions 20–24 are provided on the segment 16 and contain the medicament of the type described. When positioned, the first through third regions 20–24 contact the area to be treated. When the wrap 10 is constricted, the constricted pressure urges the regions 18 to dispense their medicament to the areas to be treated for the soothing, analgesic or anesthetic effect thereof. Furthermore, the opaque segment 16 prevents light from reaching the eyes and therefore treats photosensitivity. The pressure exerted by the wrap 10 may also provide some treatment of the pain symptoms.

As originally dispensed to the patient, the regions 20–24 may have a tear away cover to retain the medicament therein and prevent evaporation thereof. Prior to positioning the wrap 10, the covers are removed.

With reference to FIGS. 3 and 4, a further embodiment of the wrap 10 according to the present invention is shown. Like components carry like reference numerals.

According to the this embodiment, each of the segments 16 includes barriers 26 located between the first and second regions 20, 22 and the eyes when the wrap 10 is positioned about the head. These barriers 26 are resilient and manufactured from rubber or any other suitable, waterproof material and are adapted to resist medicament contained in the first and second regions 20, 22 from migrating and flowing to the eyes. While the barriers 26 are illustrated as upstanding, arcuate walls, it is to be understood that the barriers 26 could be round in cross-section or any other suitable shape.

When the wrap 10 is positioned about the head and secured, the barriers 26 engage the face proximate the orbits of the eyes and elastically deform to permit the first and second regions 20, 22 to contact the areas of the face and dispense their medicament. The barriers 26 form, with the skin, a seal to resist the medicament from flowing to the eyes.

It is to be understood, that while not illustrated in FIGS. 3 and 4, third regions 24 (FIG. 1) could also be provided on the segment 16 and may include medicament. Without medicament, the third regions 24 would be adapted to provide pressure on the eyes for purposes of the relieving pain and eye strain. Furthermore, the third regions 24 would also act as a cover to resist medicament from entering the eyes from the first and second regions 20, 22.

Either embodiment of the wrap 10 and its regions 20–24 are suitable to be pre-heated or chilled prior to application as by microwave heating or refrigeration.

While I have shown and described certain embodiments of the present invention, it is to be understood that it is subject to many modifications and changes without departing from the spirit and scope of the claims set forth herein.

I claim:

1. A device to be disposed about the head and over the eyes, supraorbital and infraorbital areas and nose bridge for treating human ailments comprising:

a wrap adapted to be disposed around the head, said wrap including an opaque, flexible segment adapted to be positioned to substantially overlay the eyes, bridge of the nose, the supraorbital region and infraorbital region;

means for tightening and securing the wrap about the head with said segment in said position;

a pair of absorbent first regions secured to said segment to project therefrom and each located, when the wrap is secured to the head, to contact said areas proximate the supraorbital region over each eye, each region adapted to be loaded with a medicament, tightening of the wrap causing said regions to exert pressure on and dispense medicament to treat the contacted area; and a barrier raised from the segment and located proximate the margin of each first region nearest the eyes, each barrier adapted to seal against the skin to resist medicament dispensed from the first region from contacting the eyes.

2. The device of claim 1 including a pair of second regions each located to contact said area proximate the infraorbital region below each eye.

3. The device of claim 2 including a barrier raised from the segment and located proximate the margin of each second region nearest the eyes, each barrier adapted to seal against the skin to resist medicament dispensed from the second regions from contacting the eyes.

4. The device of claim 3 including third regions to overlay the eyes.

5. The device of claim 4 wherein said third regions are resilient to closely cover the eyes to resist medicament retained by said first and second regions from contacting the eyes.

6. The device of claim 4 wherein said third regions are absorbent and retain water.

7. The device of claim 4 wherein said third regions are absorbent and retain a medicament.

8. A device to be disposed about the head over the eyes, nose and supraorbital and infraorbital areas of the face for treating human ailments comprising:

a wrap adapted to be disposed around the head, said wrap including an opaque, flexible segment adapted to overlay the eyes, bridge of the nose, supraorbital and infraorbital areas;

means for tightening and securing the wrap about the head with the segment in said overlay position;

absorbent first regions containing a medicament and disposed on the segment to project therefrom and located, when the wrap is tightened and secured to the head to contact and exert pressure upon and dispense medicament to the skin of said supraorbital areas;

absorbent second regions containing a medicament and disposed on the segment to project therefrom and located, when the wrap is tightened and secured to the head to contact and exert pressure upon and dispense medicament to the skin of said infraorbital areas;

absorbent third regions containing a medicament and disposed on the segment to project therefrom and located, when the wrap is tightened and secured to the head to contact and exert pressure upon and dispense medicament to the areas of said eyes: and barriers adjacent said first and second regions to resist medicament retained thereby from contacting the eyes.

9. The device of claim 8 wherein the barriers are resilient and project from the segment to seal against the skin to resist the flow of dispensed medicament to the eyes.

10. The device of claim 8 wherein the first and second medicaments are selected from a group consisting of skin applied analgesics, anesthetics and water.

11. A device to be disposed about the head and over the eyes, supraorbital and infraorbital areas and nose bridge for treating human ailments comprising:

a wrap adapted to be disposed around the head, said wrap including an opaque, flexible segment adapted to be positioned to substantially overlay the eyes, bridge of the nose, the supraorbital region and infraorbital region;

means for tightening and securing the wrap about the head with said segment in said position;

a pair of absorbent first and second regions secured to said segment to project therefrom and each located, when the wrap is secured to the head, to contact said areas proximate the supraorbital region over and the infraorbital region under each eye, each region adapted to be loaded with a medicament, tightening of the wrap causing said regions to exert pressure on and dispense medicament to treat the contacted area; and a barrier raised from the segment and located proximate the margin of each second region nearest the eyes, each barrier adapted to seal against the skin to resist medicament dispensed from the first region from contacting the eyes.

* * * * *